United States Patent [19]
Utterberg

[11] Patent Number: 5,881,774
[45] Date of Patent: *Mar. 16, 1999

[54] MEDICAL CONNECTOR WITH INTEGRAL CLOSURE

[75] Inventor: David S. Utterberg, Seattle, Wash.

[73] Assignee: Medisystems Technology Corporation, Las Vegas, Nev.

[*] Notice: The term of this patent shall not extend beyond the expiration date of Pat. No. 5,385,372.

[21] Appl. No.: 783,689

[22] Filed: Jan. 15, 1997

Related U.S. Application Data

[63] Continuation of Ser. No. 573,478, Dec. 15, 1995, abandoned.

[51] Int. Cl.⁶ .......................... F16L 55/115; B65D 51/04
[52] U.S. Cl. .......................... 138/89; 215/235; 215/306; 220/337; 604/263; 138/96 R
[58] Field of Search ........................ 138/89, 89.1–89.4, 138/96 T, 96 R; 220/339, 335, 306; 215/235

[56] References Cited

U.S. PATENT DOCUMENTS

| | | | |
|---|---|---|---|
| 2,111,186 | 3/1938 | Jenks | 222/498 |
| 2,690,861 | 10/1954 | Tupper | 222/498 |
| 3,199,748 | 8/1965 | Bross | 222/517 |
| 3,416,712 | 12/1968 | Shastal | 222/541.5 |
| 3,633,586 | 1/1972 | Sheridan | 128/207.15 |
| 3,741,217 | 6/1973 | Clarke | 128/349 X |
| 4,244,495 | 1/1981 | Lorscheid et al. | 222/153.14 |
| 4,386,714 | 6/1983 | Roberto et al. | 220/335 X |
| 4,534,483 | 8/1985 | Kassis et al. | 215/306 |
| 4,615,462 | 10/1986 | Sacherer et al. | 220/335 X |
| 4,619,651 | 10/1986 | Kopfer et al. | 604/415 |
| 4,655,363 | 4/1987 | Neat | 220/268 |
| 4,674,640 | 6/1987 | Asa et al. | 215/230 |
| 4,687,129 | 8/1987 | Cugley | 220/339 X |
| 4,713,219 | 12/1987 | Gerken et al. | 422/102 |
| 4,778,071 | 10/1988 | Fillmore | 220/335 X |
| 4,781,697 | 11/1988 | Slaughter | 604/192 |
| 4,790,567 | 12/1988 | Kawano et al. | 285/24 |
| 4,793,501 | 12/1988 | Beck | 220/339 X |
| 4,793,502 | 12/1988 | Beck | 220/339 X |
| 4,813,560 | 3/1989 | Begley | 220/339 X |
| 4,817,991 | 4/1989 | Frentzel et al. | 285/7 |
| 4,943,017 | 7/1990 | Ennis | 215/396 X |
| 4,963,132 | 10/1990 | Gibson | 604/256 |
| 4,982,842 | 1/1991 | Hollister | 206/365 |
| 5,037,000 | 8/1991 | Selame | 220/339 X |
| 5,047,021 | 9/1991 | Utterberg | 604/283 |
| 5,065,783 | 11/1991 | Ogle, II | 137/68.1 |
| 5,071,413 | 12/1991 | Utterberg | 604/283 |
| 5,078,693 | 1/1992 | Shine | 604/192 |
| 5,088,996 | 2/1992 | Kopfer et al. | 604/415 |
| 5,098,405 | 3/1992 | Peterson et al. | 604/247 |
| 5,098,410 | 3/1992 | Kerby et al. | 604/256 |
| 5,200,153 | 4/1993 | Carr et al. | 220/339 X |
| 5,213,226 | 5/1993 | Nichols | 220/263 |
| 5,221,017 | 6/1993 | Cistone et al. | 220/335 X |
| 5,225,165 | 7/1993 | Perlman | 422/102 |
| 5,233,979 | 8/1993 | Strickland | 128/207.14 |
| 5,242,417 | 9/1993 | Paudler | 604/192 |
| 5,254,314 | 10/1993 | Yu et al. | 422/102 |
| 5,259,843 | 11/1993 | Watanabe et al. | 604/256 |
| 5,382,408 | 1/1995 | Perlman | 422/102 |
| 5,385,272 | 1/1995 | Utterberg | 285/332 |

FOREIGN PATENT DOCUMENTS

| | | |
|---|---|---|
| 0 460 821 A1 | 5/1991 | European Pat. Off. . |
| WO 92/11884 | 7/1992 | WIPO . |

*Primary Examiner*—Patrick F. Brinson
*Attorney, Agent, or Firm*—Gerstman, Ellis & McMillin, Ltd.

[57] ABSTRACT

A connector for blood or solution sets (including dialysis solution sets) comprises a tube having an open outer end. The tube carries a side arm which extends radially outwardly from the tube. A cap is connected to the side arm by typically an integral plastic living hinge in a position permitting said cap to pivot between a closed position in which said cap closes the open, outer end, and an open position in which the cap is spaced from the open, outer end. The side arm defines an effectively rigid, fixed configuration to position the hinge and cap at a position permitting a directed path of motion between the open position and the closed position.

19 Claims, 1 Drawing Sheet

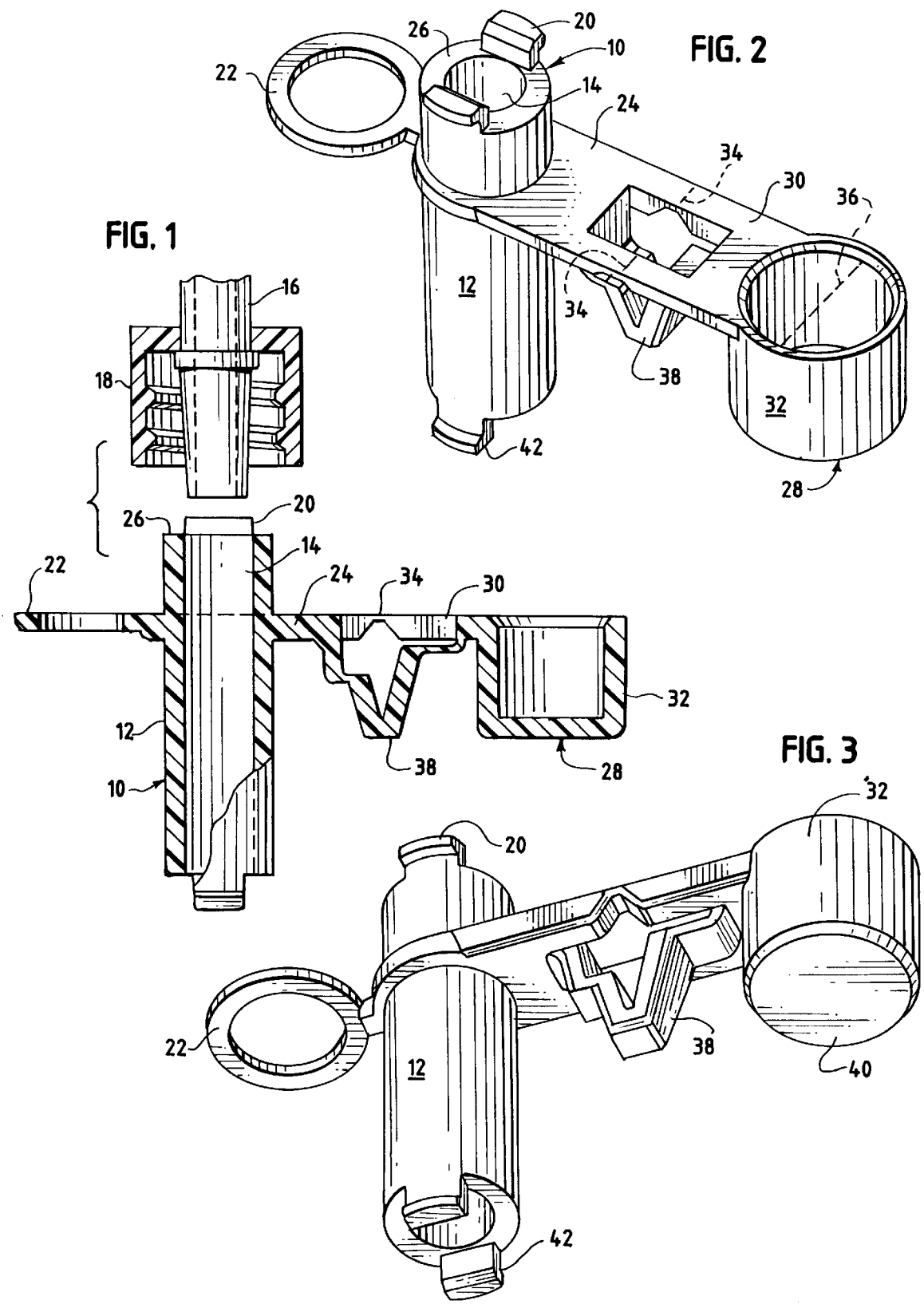

MEDICAL CONNECTOR WITH INTEGRAL CLOSURE

This is a continuation of U.S. application Ser. No. 08/573,478, filed Dec. 15, 1995 now abandoned.

BACKGROUND OF THE INVENTION

As described in Utterberg U.S. Pat. No. 5,385,372, issued Jan. 31, 1995, luer connectors are well-known and used in a wide variety of medical sets and the like, in which a tapered sleeve or nozzle fits into a tapered socket to provide a tight connection. Typically, the luer connector complies with ISO/ANSI specifications. A variant of this is the "luer-lock" connector, in which the conventional luer connection is reinforced with a releasable locking system to avoid accidental separation.

Female luer connectors in the prior art have closure caps, either separate, or attached with a flexible, umbilical cord-like strap to prevent loss of the cap.

As described in the above patent, problems with the prior art systems include the fact that when the connector is uncapped, the cap is free to move in any direction that its flexible cord or strap permits. Thus, due to such flexibility, this system is ill suited for automated capping. Manual labor is typically required to initially place the cap on the end of the connector after molding, even through the cap and connector may be simultaneously molded in a single shot. Also, when the user has removed the cap and desires to recap it, the recapping is not easily done with a single finger of the same hand holding the connector. Rather, closer attention is typically required, along with grasping of the cap with the thumb and forefinger of the other hand, to properly position the cap for recapping on the luer.

By this invention, a new design of luer connector with a hinged cap is provided. In preferred embodiments, the hinged cap may be removed from the luer connector with the action of a single finger of the same hand holding the luer connector, and it may be reapplied in a reliable, repetitive manner with a single finger as well. Additionally, the cap may be closed onto its luer connector by a machine in automated manner after molding of the cap and connector in a single shot, for a reduction of initial manufacturing costs. Nevertheless, a space is provided so that a male luer lock connector or the like may connect with the female connector of this invention, with a locking sleeve of the typical luer lock connector engaging in unimpeded manner with the exterior of the female luer connector.

The invention of this application may also be used in conjunction with connectors other than luer connectors as desired.

The connector also exhibits certain improvements over the connectors disclosed in the previously cited patent in terms of ease of molding and consequent manufacturing cost.

DESCRIPTION OF THE INVENTION

By this invention, a connector is provided which comprises a tube having an open, outer end. The tube carries a side arm which is attached to the tube at a position which is longitudinally spaced proximally from the open, outer end. The side arm extends from that position radially outwardly from the tube. Typically, the side arm is substantially rigid to occupy a single, stationary position relative to the tube to which it is attached.

A cap for closing the open end of the tube is connected to the side arm, typically by a plastic living hinge line. This hinge line and its position on the side arm are positioned to permit the cap to pivot between a closed position in which the cap closes or covers the open, outer end, and an open position in which the cap is spaced from the open, outer end. Also, the hinge is typically positioned proximal to the open, outer end, with the side arm defining an effectively rigid, fixed configuration to position the hinge and cap.

Typically, at least a portion of the cap may have a slightly larger inner diameter (for example up to about 3 mm. larger) than the outer diameter of the open, outer end of the tube, which permits the cap to fit onto and cover the end of the tube while still providing a well known tortuous pathway for gas or autoclave sterilization, even though the hinge is positioned proximal to the open, outer end. Alternately, the cap may seal the open end, as may be desirable if radiation sterilization is employed. To further facilitate closure and/or sealing, a spring member may urge the cap into closed position, for example an integrally molded spring member which may be of the known fall-through center type, or any other desired type.

Accordingly, a cap closure which has the advantages described above may also have the added advantages of being molded with improved ease, and held by spring action in its desired closed position, as well as being held in a snap-open position if desired, for an effective closure which may be open and closed by machinery if desired, or by a single finger of the user.

DESCRIPTION OF THE DRAWINGS

In the drawings,

FIG. 1 is a mostly longitudinal sectional view of the connector of this invention and the integral closure cap, shown about to connect with a conventional male luer lock connector;

FIG. 2 is a top perspective view of the connector of FIG. 1; and

FIG. 3 is a bottom perspective view of the connector of FIG. 1.

DESCRIPTION OF SPECIFIC EMBODIMENTS

Referring to the drawings, connector 10 may be used as a connector on the end of a medical set for conveying either solution or blood, comprising basically a tube 12 which has a bore 14 of female luer shape, to permit connection with a conventional male luer or luer lock connector 16, which may be connected to another set for blood or medical solution. Locking sleeve 18 of male connector 16 may engage the ears 20 carried on the distal end of tube 12. Generally, the connector as shown herein is similar to the connector of the previously cited U.S. Pat. No. 5,385,372 both in structure and contemplated use, except as otherwise indicated herein.

Connector 10 also carries a hanging member 22, for hang the tube set on an IV pole, the entire connector 10 as shown being an integral structure which may be molded in a single shot.

Connector 10 carries a integral, substantially rigid side arm 24 extending laterally out from tube 12 from a position which is longitudinally spaced from the open outer end 26 of connector 10. A cap 28 is provided, being integrally connected to side arm 24 by a cap side arm portion 30, which projects laterally from the tubular cap portion 32 of cap 28, the connection between cap 28 and side arm 24 being through an integral plastic living hinge 34. Thus, cap 28 can be pivoted to rotate toward tube 12 by about 180 degrees from the position shown to close off outer end 26 of the connector. To facilitate this, cap portion 32 may be made of fairly thin walls so as to exhibit a measure the flexibility. Also, the cap inner diameter 36 is preferably larger than the outer diameter of tube 12 by an amount as is needed to permit cap 28 to extend over the outer end 26 of tube 12 into a closed position, for example 9 mm. when tube 12 has an outer diameter of 6.7 mm. Side arm 24 and cap side arm portion 30 are of substantially equal lengths.

To facilitate the closing and opening between outer end of tube 12 and tubular cap 28, an integral plastic spring 38 of known design is shown. Spring 38 serves to hold cap 28 in either of its two normal positions, fully opened as shown, or fully closed, where cap member 32 is snugly secured about the end 26 of tubing 12. As is known, this type of integral plastic spring 38, as well as a variety of other known types, biases the system either into the fully opened or fully closed configurations with a snap action. Thus, particularly in the closed position, cap 32 is urged downwardly so that ears 20 preferably press against the end wall 40 of cap portion 32, for reliable closure of the system. Also, the system may be reliably snapped between the fully closed and the fully opened position by robotic arms or by a single finger of the user, to achieve advantages similar to those as described in the previously cited U.S. Pat. No. 5,385,372.

The lower, outwardly projecting members 42 of tube 12 may be used to connect with a male luer lock connector for reasons as described in the previously cited patent. Also, flexible plastic tubing may be conventionally sealed to tube 12 to mount it on a blood or solution set, or other medical equipment as may be desired.

The above has been offered for illustrative purposes only, and is not intended to limit the scope of the invention of this application, which is as defined in the claims below.

That which is claimed:

1. A connector which comprises a tube having an open, outer end, said tube carrying a tube side arm which is attached to said tube at a position longitudinally spaced from the open, outer end by a distance sufficient to permit a locking sleeve of another connector to surroundingly engage and lock to said tube, said tube side arm extending from said position radially outwardly from said tube; a cap having a cap side arm projecting from said cap and connected to said tube side arm by a himge in a position permitting said cap and cap side arm to pivot between a closed position in which said cap covers said open, outer end, and an open position in which the cap is spaced from said open, outer end, said tube carrying a plurality of circumferentially spaced ears adjacent to said open, outer end to engage the locking sleeve of said other connector for locked securance thereto; the tube side arm defining a substantially rigid, fixed configuration relative to said tube to position said hinge, said hinge being laterally and longitudinally spaced from said open, outer end.

2. The connector of claim 1 in which said cap has a larger inner diameter than the outer diameter of the open outer end of the tube.

3. The connector of claim 2 in which a spring member urges said cap into said closed position.

4. The connector of claim 3 in which said spring member is of the fall-through center type.

5. The connector of claim 1 in which a spring member urges said cap into said closed position.

6. The connector of claim 5 in which said spring member is of the fall-through center type.

7. The connector of claim 1 which further comprises a hanging member extending outwardly from said tube.

8. The connector of claim 7 in which said cap has a larger inner diameter than the outer diameter of the open outer end of the tube.

9. The connector of claim 1 in which said cap is flexible.

10. The connector of claim 1 in which said cap side arm and said tube side arm are of substantially equal length.

11. The connector of claim 2 in which said cap side arm and tube side arm are of substantially equal length.

12. A connector which comprises a tube having an open, outer end, said tube carrying a tube side arm which is attached to said tube at a pposition longitudinally spaced from the open, outer end by a distance sufficient to permit a locking sleeve of another connector to surroundingly engage and lock said tube, said tube side arm extending from said position radially outwardly from said tube; a flexible cap having a cap side arm projecting from said cap and connected to said tube side arm by a hinge in a position permitting said cap and cap side arm to pivot between a closed position in which said cap covers said open, outer end, and an open position in which said cap is spaced from said open, outer end, the tube side arm defining a substantially rigid, fixed configuration relative to said tube to position said hinge, said himge being positioned proximally of said open, outer end, said cap having a larger inner diameter than the outer diameter of the open, outer end of said tube to define, when closed, a tortuous, open pathway for gas or autoclave sterilization.

13. The connector of claim 12 in which a spring member urges said cap into said closed position.

14. The connector of claim 13 in which said spring member is of the fall-through center type.

15. The connector of claim 14 which further comprises a hanging member extending outwardly from said tube.

16. A connector which comprises a tube having an open, outer end, said tube carrying a tube side arm which is attached to said tube at a position longitudinally spaced from the open, outer end by a distance sufficient to permit a locking sleeve of another connector to surroundingly engage and lock said tube, said tube carrying a plurality of circumferentially spaced ears adjacent said open, outer end, to engage the locking sleeve of said other connector for locked securance thereto, said tube side arm extending from said position radially outwardly from said tube; a flexible cap having a cap side arm projecting from said cap and connected to said tube side arm by a hinge in a position permitting said cap and cap side arm to pivot between a closed position in which said cap covers said open, outer end and an open position in which the cap is spaced from said open, outer end, the tube side arm defining a substantially rigid, fixed configuration relative to said tube to position said hinge, said hinge being laterally and longitudinally spaced from said open, outer end, said cap having a larger inner diameter than the outer diameter of the open, outer end of said tube to define, when closed, a tortuous, open pathway for gas or autoclave sterilization.

17. The connector of claim 16 in which a spring member urges said cap into said closed position.

18. The connector of claim 16 in which said spring member is of the fall-though center type.

19. The connector of claim 1 in which said cap has a larger inner diameter than the outer diameter of the open, outer end of said tube.

* * * * *